US009700657B2

(12) United States Patent
Kühn et al.

(10) Patent No.: US 9,700,657 B2
(45) Date of Patent: Jul. 11, 2017

(54) BIO-ABSORBABLE COMPOSITE MATERIALS CONTAINING MAGNESIUM AND MAGNESIUM ALLOYS AS WELL AS IMPLANTS MADE OF SAID COMPOSITES

(71) Applicants: HERAEUS MEDICAL GMBH, Wehrheim (DE); MEDIZINISCHE UNIVERSITÄT GRAZ, Graz (AT)

(72) Inventors: Klaus-Dieter Kühn, Felsberg (DE); Annelie Weinberg, Schüttorf (AT); Peter Uggowitzer, Ottenbach (CH); Sebastian Vogt, Erfurt (DE); Jörg Löffler, Greifensee (CH)

(73) Assignees: HERAEUS MEDICAL GMBH, Wehrheim (DE); MEDIZINISCHE UNIVERSITÄT GRAZ, Graz (AT)

( * ) Notice: Subject to any disclaimer, the term of this patent is extended or adjusted under 35 U.S.C. 154(b) by 0 days.

(21) Appl. No.: 14/337,492

(22) Filed: Jul. 22, 2014

(65) Prior Publication Data
US 2015/0032201 A1    Jan. 29, 2015

(30) Foreign Application Priority Data
Jul. 26, 2013    (DE) .................. 10 2013 214 636

(51) Int. Cl.
*A61L 31/12*    (2006.01)
*A61F 2/88*    (2006.01)
(Continued)

(52) U.S. Cl.
CPC .......... *A61L 31/124* (2013.01); *A61F 2/885* (2013.01); *A61L 27/047* (2013.01); *A61L 27/54* (2013.01);
(Continued)

(58) Field of Classification Search
CPC .................................. A61F 2/88; A61F 2/82
See application file for complete search history.

(56) References Cited

U.S. PATENT DOCUMENTS

| 4,206,516 A | 6/1980 | Pilliar |
| 7,279,175 B2 | 10/2007 | Chen et al. |
| (Continued) | | |

FOREIGN PATENT DOCUMENTS

| CN | 1589166 A | 3/2005 |
| CN | 101249286 A | 8/2008 |
| (Continued) | | |

OTHER PUBLICATIONS

Won-Wook Park, Bong-Sun You, Byoung-Gi Moon & Wan-Chul Kim, Jun. 14, 1999, Science and Technology of Advanced Materials, II, 73-78.*

(Continued)

*Primary Examiner* — Thomas J Sweet
*Assistant Examiner* — Wade P Schutte
(74) *Attorney, Agent, or Firm* — Norris McLaughlin & Marcus PA

(57) ABSTRACT

The invention relates to a composite material that comprises at least one magnesium component, whereby the magnesium component consists of pure magnesium or a magnesium-calcium alloy or a magnesium-calcium-X alloy, whereby X is another biodegradable element. The composite material also contains at least one organic anti-infective agent having a solubility in water at room temperature of less than 10 grams per liter.

19 Claims, 2 Drawing Sheets

(51) Int. Cl.
*A61L 27/04* (2006.01)
*A61L 27/54* (2006.01)
*A61L 27/58* (2006.01)
*A61L 31/02* (2006.01)
*A61L 31/14* (2006.01)
*A61L 31/16* (2006.01)
*C22C 21/06* (2006.01)

(52) U.S. Cl.
CPC ............ *A61L 27/58* (2013.01); *A61L 31/028* (2013.01); *A61L 31/148* (2013.01); *A61L 31/16* (2013.01); *A61F 2220/005* (2013.01); *A61L 2300/206* (2013.01); *A61L 2300/23* (2013.01); *A61L 2300/406* (2013.01); *A61L 2300/414* (2013.01); *C22C 21/06* (2013.01)

(56) References Cited

U.S. PATENT DOCUMENTS

| | | |
|---|---|---|
| 2003/0108588 A1 | 6/2003 | Chen et al. |
| 2005/0107870 A1* | 5/2005 | Wang ................. A61L 31/10 623/1.44 |
| 2006/0073198 A1* | 4/2006 | Boni ..................... A61K 9/0078 424/450 |
| 2006/0088596 A1* | 4/2006 | Labrecque ............ A61L 31/148 424/472 |
| 2007/0009557 A1 | 1/2007 | Kuhn et al. |
| 2007/0213827 A1 | 9/2007 | Arramon |
| 2007/0213832 A1* | 9/2007 | Wen .............................. 623/23.5 |
| 2008/0131479 A1* | 6/2008 | Weber et al. ................. 424/426 |
| 2008/0161906 A1* | 7/2008 | Atanasoska ........... A61L 31/022 623/1.38 |
| 2008/0161907 A1 | 7/2008 | Chen et al. |
| 2008/0177378 A1 | 7/2008 | Asgari |
| 2008/0195189 A1 | 8/2008 | Asgari |
| 2009/0081313 A1 | 3/2009 | Aghion et al. |
| 2009/0131540 A1* | 5/2009 | Hiromoto .............. A61L 27/047 514/769 |
| 2009/0240323 A1 | 9/2009 | Wilcox |
| 2010/0075162 A1* | 3/2010 | Yang et al. .................... 428/457 |
| 2011/0027188 A1 | 2/2011 | Kleiner et al. |
| 2011/0076319 A1 | 3/2011 | Orlowski et al. |
| 2012/0209402 A1 | 8/2012 | Ip et al. |
| 2014/0154341 A1 | 6/2014 | Manuel et al. |

FOREIGN PATENT DOCUMENTS

| | | |
|---|---|---|
| CN | 101516292 A | 8/2009 |
| CN | 102014978 A | 4/2011 |
| WO | 03/024455 A2 | 3/2003 |
| WO | 2008/035948 A1 | 3/2008 |
| WO | 2008 087215 A2 | 7/2008 |
| WO | 2012 003502 A2 | 1/2012 |
| WO | 2013 052791 | 4/2013 |

OTHER PUBLICATIONS

Salahshoor et al.; "Biodegradable Orthopedic Magnesium-Calcium (MgCa) Alloys, Processing, and Corrosion Performance"; Materials 2012, 5, pp. 135-155.

European Search Report dated Jan. 12, 2015 from corresponding European Application.

Patent Examination Report No. 1 issued Nov. 14, 2014 in corresponding Australian Application 2014204442.

Chinese Notification of the First Office Action issued in corresponding CN Application 2014103600619 on Oct. 22, 2015 and English translation.

Canadian Office Action for corresponding application CA 2,856,990 dated Sep. 8, 2016.

* cited by examiner

BIO-ABSORBABLE COMPOSITE MATERIALS CONTAINING MAGNESIUM AND MAGNESIUM ALLOYS AS WELL AS IMPLANTS MADE OF SAID COMPOSITES

This application claims priority of German Patent Application No. DE 10 2013 214 636.2, filed Jul. 26, 2013, the entire contents of which are incorporated herein by reference.

The present invention relates to bio-absorbable composite materials containing magnesium and magnesium alloys, in particular magnesium-calcium alloys, as well as implants made of said composites.

Unlike polymer materials, which usually show relatively poor mechanical properties, and ceramic materials, which possess low ductility and toughness, metallic materials offer good mechanical properties altogether such that in-vivo degradable metal-based materials are becoming conceivable for medical applications to an increasing degree.

Aside from other metals, in particular magnesium and magnesium alloys are being used. Said materials are ideal in that their elastic properties are equivalent to those of bone such that no tension arises between implants made of said materials and the existing bone when a mechanical stress acts on them.

Magnesium-calcium alloys and their properties for medical applications are described in Materials 2012, 5, 135-155 (www.mdpi.com/journal/materials, open access), "Biodegradable Orthopedic Magnesium-Calcium (MgCa) Alloys, Processing, and Corrosion Performance" by Meisam Salahshoor and Yuebin Guo. As illustrated in said reference, the use of magnesium or magnesium alloys as bio-absorbable implants is associated with a problem, firstly due to a high degradation rate and secondly due to hydrogen being produced during the degradation of magnesium. Due to the high degradation rate and the formation of large amounts of hydrogen, which cannot be taken up by the body at an appropriate rate, there is a danger of sub-cutaneous gas pockets being generated. Moreover, the rapid corrosion of magnesium leads to early loss of mechanical integrity.

It is therefore the object of the present invention to provide a material that shows the advantageous properties of magnesium and magnesium alloys, but compensates for the disadvantages thereof.

Surprisingly, it has been evident that composite materials made of pure magnesium or magnesium alloys and comprising one or more anti-infective agents having a solubility in water at room temperature (25° C.) of less than 10 mg/l solve said object.

BRIEF DESCRIPTION OF THE DRAWINGS

The invention will now be described in greater detail with reference to the drawings, wherein.

Figure 1:
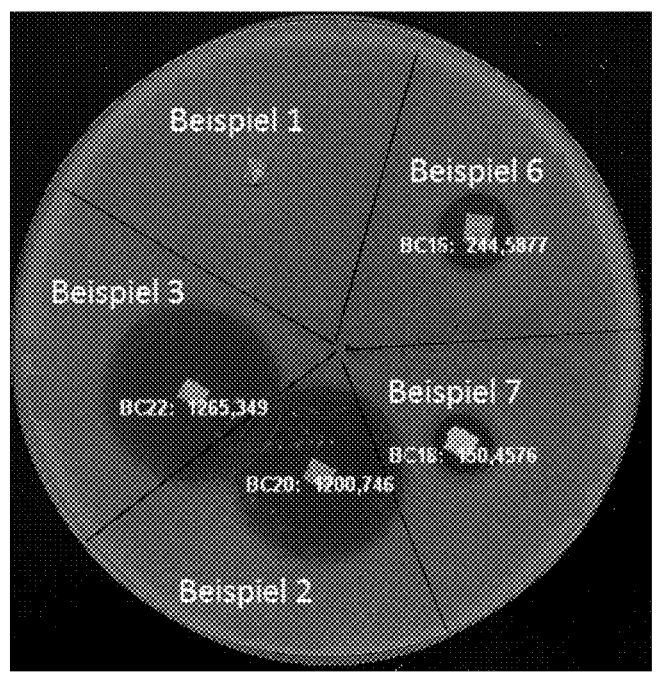
FIG. 1 shows the formation of inhibition zones in examples 1, 2, 3, 6, and 7.

Magnesium according to the invention or a magnesium alloy according to the invention is preferable made from highly pure magnesium as the starting substance. For this purpose, the purity of, for example, commercially available magnesium of conventional purity (99.8%; available, e.g., from AMAG Austria Metall AG, A) is increased to a purity in excess of 99.99% by means of vacuum distillation. Instead of pure magnesium, is also feasible to use magnesium alloys, preferably magnesium-calcium alloys, which can be produced in a protective gas from highly pure magnesium and a further biocompatible metal (e.g. calcium, zinc) according to known methods. Subsequent tempering and extrusion steps serve to improve the mechanical properties of the magnesium-calcium alloys or magnesium-calcium-X alloys, whereby X is a further biocompatible and biodegradable element, by means of a specific change of their micro-structure. Other forming methods according to the prior art are also feasible as long as the purity of the materials is maintained.

It is preferable for the magnesium component of the composite material to consist of pure magnesium having a total impurities content of less than 0.05% by weight, preferably of less than 0.01% by weight, or to consist of a magnesium-calcium alloy having a calcium content ranging from trace amounts (i.e. from 1 ppm, preferably from 10 ppm) to the eutectic point of the alloy (i.e. 16.2% by weight). Magnesium-calcium alloys of structural type C14 (Laves phase, stoichiometry Mg2Ca) are particularly preferred. These are formed by heat treatment below 400° C. and serve for grain refinement and thus for improvement of the mechanical properties. Since calcium is less noble than magnesium, this phase does not act in cathodic manner, but rather is dissolved in aqueous solution (e.g. in body fluids, such as blood) in anodic manner and thus leaves behind the "undisturbed" magnesium surface. It is particularly preferable for the calcium content of the magnesium alloy to be between 0.1% by weight and 1% by weight, in particular between 0.2% by weight and 0.6% by weight. In particular, the total content of biologically questionable impurity elements (e.g. rare earth elements, aluminium, copper) in all alloys is to be less than 50 ppm, preferably less than 10 ppm. Biologically questionable impurity elements in the scope of the invention are elements that have a toxic effect on the body (e.g. Be, Pb, Hg, As, Cr, Cu), can elicit allergic reactions (e.g. Ni, Co, Cr), show a carcinogenic effect (e.g. Cr compounds) or are suspected of eliciting diseases (e.g. Al).

The composite material according to the invention comprises a poorly water-soluble organic anti-infective agent. This means that the solubility of the anti-infective agent at 25° C. is less than 10 g per litre. Preferably, the solubility of the anti-infective agent in water is less than 2 g per litre. The low solubility of the agent in water results in a delayed dissolution of the agent under in-vivo conditions. As a result, the agent is released into the organism slowly and over an extended period of time and at relatively low concentrations. Simultaneously, the absorption of the magnesium component of the composite is delayed; the formation of hydrogen proceeds over a longer period of time.

Basically, any anti-infective agent is well-suited provided its solubility in water is less than 10 g per litre of water at 25° C. The anti-infective agent can be selected from the group of substances with an activity against bacteria, fungi, and viruses or a mixture thereof. Anti-infective agents to be used according to the invention are directed against germs that are pathological in particular for humans, for example against gram-positive germs such as *Staphylococcus aureus, Staphylococcus albus,* and *Streptococcus,* gram-negative germs such as *Escherichia coli, Bacterium proteus, Pseudomonas, Enterococcus,* and *Klebsiella.*

Examples of well-suited antibiotics include antibiotics from the group of aminoglycosides, lincosamides, glycopeptides, polymyxins, oxazolidinones. According to the invention, the antibiotics can be present in any form, in which the antibiotic has anti-infective efficacy or which enables the release of a compound having an anti-infective effect. The term, antibiotics, therefore also encompasses antibiotics salts or antibiotics esters as well as the corresponding hydrated forms of the antibiotics, antibiotics salts or antibiotics esters. It is preferable to use poorly soluble fatty acid salts of aminoglycosides. Pertinent examples include gentamicin myristate, gentamicin palmitate, gentamicin stearate, tobramycin myristate, tobramycin palmitate, tobramycin stearate, amikacin myristate, amikacin palmitate, amikacin stearate, vancomycin palmitate, vancomycin stearate, ramoplanin palmitate, ramoplanin stearate, levofloxacin palmitate, levofloxacin stearate, ofloxacin palmitate, ofloxacin stearate, moxifloxacin palmitate, moxifloxacin stearate, clindamycin palmitate, and clindamycin stearate. The terms, palmitate, stearate, and myristate, shall be understood to refer to the antibiotics salts of palmitic acid, stearic acid, and myristic acid. The preferred molar ratio of protonated amino group to fatty acid anion in this context is equal to 1. However, it is feasible just as well that only some of the protonated amino groups have fatty acid anions for counter-ions. Accordingly, for example gentamicin pentakispalmitate, gentamicin tetrakispalmitate or gentamicin tripalmitate can be used as poorly water-soluble antibiotics salts.

Moreover, cationic and/or anionic antiseptics are also well-suited, whereby chlorhexidine, octenidine, dequalinium chloride, polyhexanide, and oligomeric biguanides are particularly preferred. Moreover, growth factors and, in particular, BMP-2, BMP-7, and proteins derived from them, neoangiogenesis-inducing proteins, steroid hormones, bisphosphonates, and antiphlogistics can be used.

The invention also relates to medical implants made from said composite material. In this context, a geometrical body made of the magnesium component can be produced first, and the anti-infective agent can then be applied to the surface of the geometrical body. However, it is feasible just as well that the geometrical body comprises pores filled with the agent. Advantageously, the size of the pores is appropriate such that a surface structure remains even after coating in order to optimise osseointegration. Implants, in which the magnesium component is particulate and made up of particles with a diameter of less than 100 µm, preferably less than 50 µm, are conceivable as well. Moreover, magnesium component and anti-infective agent can also be present in composites that are made up of, for example, multiple layers.

Preferably, the anti-infective agent is present at a concentration of 0.1 to 100 mg, in particular of 1 to 10 mg per gram of absorbable implant material, depending on the concentration of the agent used and/or on which coating and/or loading method is used in order to equip the geometrical magnesium bodies.

Referring to a coating, the preferred thickness of the coating is 0.001 to 1 mm, in particular 0.01 to 0.5 mm. The surface of the magnesium body can be covered partly or fully by the anti-infective agent; preferably, the entire surface of the component of the composite is covered.

The coating can be done by means of coating methods that are conventional and known to persons skilled in the art, such as, for example, immersion or spraying methods or drops can be applied to the material bodies. For this purpose, the agent can be applied in the form of a solution or suspension. Examples of well-suited solvents comprise, e.g., alcohols, such as methanol, ethanol, etc. Solid substances can also be applied, for example, by melting them onto surfaces.

Moreover, the coating and/or loading can also be effected by means solid agents.

The geometrical body can take any shape, such as, for example, plates or wires. Surprisingly, it has been evident that the present invention is particularly well-suited for delicately structured implants, such as wires, meshes, wovens, etc.

Preferably, the composite material is used for bodies having an elongated geometry, whereby a body made of the magnesium component has an axial ratio of >500, preferably >1,000. The body is a wire in this context. Said wire preferably has a diameter of less than 500 µm, preferably of less than 200 µm, and particularly preferably of less than 100 µm.

One or more of the wires can be arranged to have any geometry. For example, two or more wires, extending as helices, can form a tube-shaped two-dimensional structure. In this context, it is preferred to arrange at least two wires in opposite directions above each other with equal or different pitch. Implants plaited in this manner, in particular stents, can be adjusted very delicately through the selection of the wires.

In this context, a tube-shaped two-dimensional structure thus formed can be mechanically interlocked in its longitudinal axis through plastic deformation. The interlocking is preferably implemented by means of at least one partial deformation of the wire towards the inside or towards the outside, whereby the curvature of the interlocking is small as compared to the circular shape of the tube-shaped two-dimensional structure.

The components of the composite material in the implant can just as well be arranged in layers. In this context, both components of the composite comprise a two-dimensional geometry. In this case, the components can be layered into a parallel composite and, if applicable, can be joined at the ends through a bonding force, a substance-to substance bond or a form-fit. In this context, individual layers of the magnesium component can comprise a perforation.

An individual layer of the magnesium component in the composite material preferably has a thickness of less than 500 µm, more preferably of less than 200 µm, particularly preferably of less than 100 µm.

In the following, the invention and its embodiments shall be illustrated in more detail on the basis of examples.

EXAMPLE A

Production of a Component of the Composite From Highly Pure Magnesium to Generate a Composite Body of a Flat Geometry The purity of magnesium of conventional purity (99.8%; source: AMAG Austria Metall AG, A) was increased to a purity of 99.998% by means of vacuum distillation (test facility of ETH Zurich). Then, the magnesium bolt produced during the distillation having a diameter of 55 mm and a length of 110 mm was turned mechanically to a diameter of 50 mm and heated to 300° C. in a resistance furnace. An extrusion facility (Müller-Engineering, Friedberg, D) was used to press the pre-heated bolt into a round profile with a diameter of 6 mm. In a further step, small plates of a geometry of 10 mm in length, 5 mm in width, and 0.25 mm in thickness were cut out of the round profile. This was done by means of wire erosion.

EXAMPLE B

Production of a Component of the Composite From a Magnesium-Calcium Alloy to Generate a Composite Body of an Extended Geometry Magnesium of high purity (99.95%; source: Alfa Aesar; Karlsruhe, D) was alloyed in a resistance furnace in a nitrogen atmosphere with SF6 additive containing 0.3% by weight calcium. Then, the billet thus produced having a diameter of 55 mm and a length of 110 mm was turned mechanically to a diameter of 50 mm and heated to 325° C. in a resistance furnace. An extrusion facility (Müller-Engineering, Friedberg, D) was used to press the pre-heated bolt into a round profile with a diameter of 6 mm. The profile was then deformed further from 6 mm to 3 mm diameter at 300° C. on a rotary swaging machine (Bock, Lüdenscheid, D). In twelve drawing steps at room temperature on a gold-smith drawing die with 10 minutes intermediary annealing at 300° C. each, a fine wire having a diameter of 0.2 mm was produced.

REFERENCE EXAMPLE 1 AND EXAMPLES 2-5

Production of Composite Bodies Through Coating of the Components of a Composite Produced in Examples A and B with Gentamicin Palmitate Firstly, a 4% methanolic gentamicin palmitate solution was prepared. For this purpose, 0.4 g gentamicin palmitate were dissolved at room temperature under stirring in 9.6 g amine-free methanol. This produces a clear, slightly yellow solution.

The small plates (1.0×0.5 cm) (examples 2 and 3) from example A and wires (length 10 cm, examples 4 and 5) from example B, which had first been heated to 90° C. and then had droplets of methanolic gentamicin palmitate solution applied to them, were used as component of the composite. The methanol evaporated instantaneously and the gentamicin palmitate formed a colourless to slightly turbid coating on the surface of the test body.

Table 1 shows the mass of the composite materials before and after coating. Reference example 1 shows an uncoated composite component.

EXAMPLES 6-9 AND REFERENCE EXAMPLE 10

Production of Composite Bodies Through Coating of the Components of a Composite Produced in Examples A and B with Octenidine/Lauric Acid Solution Firstly, a mixture containing octenidine/lauric acid was produced. For this purpose, 10.0 g lauric acid were melted in a beaker at 80° C. Then, 15.0 g octenidine hydrochloride were added. The mixture was homogenised by stirring. Then, the mixture was cooled to room temperature.

Subsequently, an octenidine/lauric acid solution was produced by dissolving 0.5 g of the mixture containing octenidine/lauric acid in 25.0 g ethanol at room temperature.

The small plates (1.0×0.5 cm) (examples 2 and 3) from example A and wires (length 10 cm, examples 4 and 5) from example B, which had first been heated to 90° C. and then had droplets of ethanolic octenidine/lauric acid solution applied to them, were used as component of the composite. The solvent evaporated instantaneously and a colourless to white-turbid coating was formed.

Table 1 shows the mass of the composite materials before and after coating. Reference example 10 shows an uncoated composite component.

TABLE 1

Overview of the coated test bodies

| Example | Material | Mass before coating [mg] | Mass after coating [mg] | Coating [mg] | Material |
| --- | --- | --- | --- | --- | --- |
| 1 | Small plate | — | — | Reference | — |
| 2 | Small plate | 23.4 | 23.9 | 0.5 | Gentamicin palmitate |
| 3 | Small plate | 22.3 | 23.1 | 0.8 | Gentamicin palmitate |
| 4 | Wire | 6.3 | 7.0 | 0.7 | Gentamicin palmitate |
| 5 | Wire | 6.0 | 8.3 | 2.3 | Gentamicin palmitate |
| 6 | Small plate | 31.4 | 31.8 | 0.4 | Octenidine/Lauric acid |
| 7 | Small plate | 23.0 | 45.7 | 22.7 | Octenidine/Lauric acid |
| 8 | Wire | 5.9 | 6.2 | 0.3 | Octenidine/lauric acid |
| 9 | Wire | 5.9 | 14.3 | 8.4 | Octenidine/lauric acid |
| 10 | Wire | — | — | Reference | — |

Figure 2:
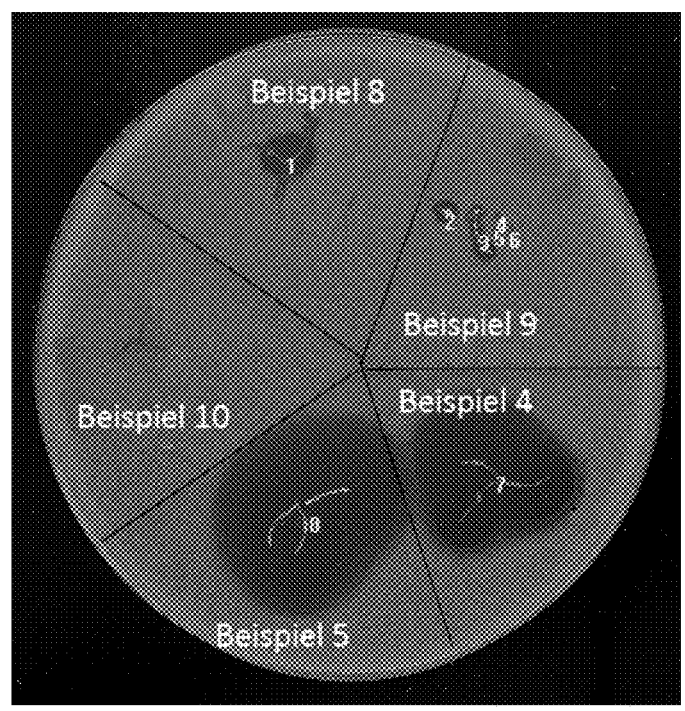
FIG. 2 shows the formation of inhibition zones in examples 4, 5, 8, 9, and 10.

The composite materials produced in the examples and reference examples were subjected to an agar diffusion test (inhibition zone test), in which sterile nutrient agar I was inoculated with spores of Bacillus subtilis ATCC 6633. The inoculated nutrient agar was then poured into sterile Petri dishes. Once the nutrient agar had cooled down, the composite materials were placed on the surface of the nutrient agar. After incubation of the test bodies for 24 hours at 37° C., the inhibition zones were scanned with a common scanner. The results are shown in Table 2. FIGS. 1 and 2 show the scanned images, whereby FIG. 1 shows the formation of inhibition zones in examples 1, 2, 3, 6, and 7 and FIG. 2 shows the formation of inhibition zones in examples 4, 5, 8, 9, and 10.

TABLE 2

Overview of the results of the microbial agar diffusion test

| Example | Material | Coating [mg] | Material | Result |
| --- | --- | --- | --- | --- |
| 1 | Small plate | Reference | — | Growth |
| 2 | Small plate | 0.5 | Gentamicin palmitate | Inhibition |
| 3 | Small plate | 0.8 | Gentamicin palmitate | Inhibition |
| 4 | Wire | 0.7 | Gentamicin palmitate | Inhibition |
| 5 | Wire | 2.3 | Gentamicin palmitate | Inhibition |
| 6 | Small plate | 0.4 | Octenidine/lauric acid | Inhibition |
| 7 | Small plate | 22.7 | Octenidine/lauric acid | Inhibition |
| 8 | Wire | 0.3 | Octenidine/lauric acid | Inhibition |
| 9 | Wire | 8.4 | Octenidine/lauric acid | Inhibition |
| 10 | Wire | Reference | — | Growth |

The invention claimed is:
1. A composite material comprising at least one magnesium component made of magnesium or a magnesium alloy, and at least one organic anti-infective agent, whereby the solubility of the anti-infective agent in water at room temperature is less than 10 grams per liter,
   in the form of a geometrical body made up of the magnesium component, and the surface of a magnesium body made of the magnesium component is partly or fully covered by the anti-infective agent, the thickness of anti-infective coating being 0.001 to 1 mm,
   wherein the magnesium component consists of pure magnesium having a total impurities content of less than 0.05% by weight or a magnesium-calcium alloy having a calcium content of 0.1 to 1.0% by weight, and the total amount of rare earth metal in the magnesium component is less than 50 ppm, wherein the anti-infective agent is present in a concentration of 0.1 to 100 mg per gram of absorbable implant material, and wherein the magnesium component of the composite material is a wire and has a diameter of less than 500 µm, or both components of the composite material comprise a two-dimensional geometry which are layered into a parallel composite and an individual layer of the magnesium component in the composite material has a thickness of less than 500 µm.

2. Composite material according to claim 1, wherein the magnesium component is a magnesium-calcium alloy having a calcium content of 0.1 to 1.0% by weight.

3. Composite material according to claim 1, wherein the total content of biologically questionable impurity elements of the magnesium component is less than 50 ppm.

4. Composite material according to claim 1, wherein the solubility of the anti-infective agent at 25° C. is <2 g/L of water.

5. Composite material according to claim 1, wherein the anti-infective agent comprises at least one antibiotic selected from the group of aminoglycoside antibiotics, lincosamide antibiotics, glycopeptide antibiotics, polymyxin antibiotics, and oxazolidinone antibiotics.

6. Composite material according to claim 5, wherein the antibiotic is a fatty acid salt of the aminoglycoside antibiotics.

7. Composite material according to claim 1, wherein the anti-infective agent comprises at least one antiseptic selected from the group consisting of cationic and anionic antiseptics and growth factors.

8. Composite material according to claim 7, wherein the antiseptic is selected from the group consisting of chlorhexidine, octenidine, dequalinium chloride, polyhexanide, oligomeric biguanides, BMP-2, BMP-7, and proteins derived from them, neoangiogenesis-inducing proteins, steroid hormones, bisphosphonates, and antiphlogistics.

9. Implant comprising a composite material according to claim 1, wherein at least one magnesium component of the composite material has an elongated geometry with a ratio of length to width of >1,000.

10. Implant according to claim 9, wherein each magnesium component forms a wire that is coiled in the form of a helix such that a tube-shaped two-dimensional structure is formed.

11. Implant according to claim 9, wherein at least two wires are coiled in opposite directions with equal or different pitch, whereby the wires are partially deformed towards the inside or the outside, in that the deformations form projections and depressions in the jacket surface of the tube-shaped two-dimensional structure such that the tube-shaped two-dimensional structure is mechanically interlocked in the longitudinal axis.

12. Implant according to claim 10, wherein the wire has a diameter of less than 200 µm.

13. Implant comprising a composite material according to claim 1, wherein both components of the composite comprise a two-dimensional geometry which are layered into a parallel composite.

14. Implant according to claim 13, wherein the individual layers are fixed to each other on their outer edges through a bonding force, a substance-to-substance bond or a form-fit.

15. Implant according to claim 13, wherein individual or all layers of the magnesium components comprise a perforation.

16. Implant according to claim 13, wherein an individual layer of the magnesium component in the composite material has a thickness of less than 200 µm.

17. Implant comprising a composite material according to claim 1, wherein the magnesium component is particulate, whereby the particles have a grain size of <100 µm.

18. Implant according to claim 12, wherein the wire has a diameter of less than 100 µm.

19. Implant according to claim 16, wherein an individual layer of the magnesium component in the composite material has a thickness of less than 100 µm.

* * * * *